(12) United States Patent
Akimoto et al.

(10) Patent No.: US 8,198,446 B2
(45) Date of Patent: Jun. 12, 2012

(54) CRYSTALLINE MICROPOWDER PARTICLES

(75) Inventors: Masahiro Akimoto, Mishima (JP);
Toshikazu Komagata, Mishima (JP);
Motohiro Shiraki, Kamakura (JP);
Akihiro Ando, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 439 days.

(21) Appl. No.: 12/601,150

(22) PCT Filed: May 20, 2008

(86) PCT No.: PCT/JP2008/059194
§ 371 (c)(1),
(2), (4) Date: Nov. 20, 2009

(87) PCT Pub. No.: WO2008/143239
PCT Pub. Date: Nov. 27, 2008

(65) Prior Publication Data
US 2010/0160634 A1 Jun. 24, 2010

(30) Foreign Application Priority Data
May 21, 2007 (JP) ................................. 2007-133691

(51) Int. Cl.
*C07D 489/08* (2006.01)
(52) U.S. Cl. ........................................................ 546/44
(58) Field of Classification Search ...................... 546/44
See application file for complete search history.

(56) References Cited

U.S. PATENT DOCUMENTS
7,718,664 B2 * 5/2010 Izumimoto et al. ........... 514/282

FOREIGN PATENT DOCUMENTS

| WO | WO 2004/033457 | 4/2004 |
|---|---|---|
| WO | WO 2005/094826 | 10/2005 |
| WO | WO 2006/049248 | 5/2006 |
| WO | WO 2007/055184 | 5/2007 |
| WO | WO 2007/072749 | 6/2007 |

OTHER PUBLICATIONS

Yoshihisa Sagawa, Iyakuhin Seizai Gijutsu, CMC Publising Co., Ltd., Jul. 25, 2002, pp. 5 to 10 (particularly, Chapter 1 Hasai Sosa: Kisohen, Ippanteki na Funsai no Hoho no tables 1, 2), pp. 25 to 34 (particularly, 1.3 Iyakuhin no Seisan Kishu to shiteno Jet Type no Hyoka (pp. 29 to 33)) (with an English language translation).
Simon et al., "Stereoselective Synthesis of β-Naltrexol, β-Naloxol, β-Naloxamine, β-Naltrexamine and Related Compounds by the Application of the Mitsunobu Reaction", Tetrahedron, vol. 50, No. 32, pp. 9757-9768, 1994.

* cited by examiner

*Primary Examiner* — Charanjit Aulakh
(74) *Attorney, Agent, or Firm* — Birch, Stewart, Kolasch & Birch, LLP

(57) ABSTRACT

Crystalline particles of N-(17-cyclopropylmethyl-4,5α-epoxy-3,14-dihydroxy-morphinan-6β-yl)-phthalimide or a pharmaceutically acceptable salt thereof are disclosed. The crystalline particles have a particle diameter distribution in which a particle diameter (D50) at the point where cumulative frequency of volume distribution cumulatively calculated from particles having a smaller diameter reaches 50% is within a range of 1 to 30 μm, and a particle diameter (D90) at the point where cumulative frequency of volume distribution cumulatively calculated from particles having a smaller diameter reaches 90% is not more than 90 μm, which crystalline particles have a degree of crystallinity of not less than 80%. By the crystalline particles, bioavailability of the active substance may be increased while ensuring storage stability of the compound.

12 Claims, 2 Drawing Sheets

CRYSTALLINE MICROPOWDER PARTICLES

TECHNICAL FIELD

The present invention relates to crystalline particles of pharmaceutically useful N-(17-cyclopropylmethyl-4,5α-epoxy-3,14-dihydroxy-morphinan-6β-yl)-phthalimide (hereinafter also referred to as "the subject compound") which are finely ground, and crystalline finely-ground particles obtained by specific fine grinding process.

BACKGROUND ART

The subject compound and its synthesis method have been already disclosed (Non-patent Literature 1). Furthermore, its therapeutic or prophylactic activity against urinary frequency or urinary incontinence, antipruritic activity, analgesic activity, therapeutic or prophylactic activity against functional bowel disorder such as irritable bowel syndrome and antitussive activity have also been already disclosed (Patent Literature 1 to 5, an antitussive activity was disclosed after the priority date of the present application).

There is a concern that the storage stability may be decreased when the subject compound disclosed in the above-mentioned literature is formulated into an injection solution, liquid formulation or the like using it as a pharmaceutical active substance, since the subject compound in a state of solutions is likely to be affected by light, heat and oxygen. Although a common method for increasing solubility rate includes a method wherein the compound is lyophilized to be an amorphous powder, there is also a concern that the storage stability may be decreased since the hygroscopicity and the specific surface area increase compared to those powders having a high crystallinity.

For these reasons, considering an easy handling of such pharmaceuticals that have a high storage stability of the subject compound or convenience for patients, oral solid preparations are desirable for the known medical uses.

However, there is a concern that sufficient oral absorption may not be obtained when oral solid preparations are made using the subject compound as a pharmaceutical active substance, since the solubility rate of the subject compound in water is low.

Therefore, it has been considered that some sort of means for increasing the solubility rate of the subject compound concurrently with ensuring the storage stability is required.

When crystalline powders having a low solubility rate in water are used as a pharmaceutical active substance, methods in which the pharmaceutical active substance is ground into a fine powder may be used so that the solubility rate of the pharmaceutical active substance increases, which results in the increased oral absorption, and thus the increased bioavailability. However, there is a high possibility that, when the crystalline powders are finely ground according to such methods, crystalline powders may lose their crystalline structure and become amorphous, which results in the decreased storage stability. Thus, selection of the fine grinding process is relevant.

As a fine grinding process, those wherein tumbler mills such as a ball mill, fluid energy mills such as a jet mill, impact mills such as a hammer mill and a pin mill are used are known. However, properties of the powders obtained after grinding vary depending on a combination of the physicochemical properties of the compounds and the selected grinding process.

Although Patent Literatures or Non-patent Literatures listed below disclose the subject compound and its use, they are completely silent about the methodology for providing an appropriate crystalline finely-ground particles of the subject compound. Therefore, these literatures do not suggest at all that the subject compound may become a more useful pharmaceutical active substance when the subject compound is grounded by a specific grinding process so as to obtain crystalline finely-ground particles having a high solubility rate and thus a remarkably high bioavailability at the same time as having an ensured storage stability.

Patent Literature 1: WO 2004/033457
Patent Literature 2: WO 2005/094826
Patent Literature 3: WO 2006/049248
Patent Literature 4: WO 2007/055184
Patent Literature 5: WO 2007/072749
Non-patent Literature 1: Simon C. et. al., Tetrahedron, 50, 9757, 1994.

DISCLOSURE OF THE INVENTION

Problems which the Invention Tries to Solve

There is a concern that the subject compound which is not finely ground yet has a low bioavailability as a pharmaceutical active substance, since the solubility rate thereof in water is low. Thus, it has been demanded to obtain appropriate crystalline finely-ground particles which have an increased solubility rate and bioavailability concurrently with ensuring the storage stability of the subject compound.

Means for Solving the Problem

In order to solve the problem above, the present inventors carried out a preliminary experiment to find that the crystallinity is drastically impaired and the storage stability as a pharmaceutical active substance is decreased when the subject compound is finely ground using a ball mill or a mortar and pestle. Then the present inventors intensively studied to find that, by using fluid energy mills or impact mills, the subject compound can be finely ground without any drastic impairment in the crystallinity, and that, by such fine grinding, crystalline finely-ground particles having a particle diameter distribution suitable for improving solubility rate and bioavailability as a pharmaceutical active substance can be obtained while ensuring the storage stability of the subject compound, thereby completing the present invention.

That is, the present invention provides crystalline particles of N-(17-cyclopropylmethyl-4,5α-epoxy-3,14-dihydroxy-morphinan-6β-yl)-phthalimide or a pharmaceutically acceptable salt thereof, having a particle diameter distribution in which a particle diameter (D50) at the point where the volume which is cumulatively measured from smaller particles reaches 50%, that is, the point where the cumulative frequency of the volume distribution reaches 50% is within a range of 1 to 30 μm, and a particle diameter (D90) at the point where the volume which is cumulatively measured from smaller particles reaches 90%, that is, the point where the cumulative frequency of the volume distribution reaches 90% is not more than 90 μm, which crystalline particles have a degree of crystallinity of not less than 80%. The present invention also provides crystalline particles of N-(17-cyclopropylmethyl-4,5α-epoxy-3,14-dihydroxy-morphinan-6β-yl)-phthalimide or a pharmaceutically acceptable salt thereof, having a particle diameter distribution in which cumulative frequency of volume distribution occupied by particles having a volume-base particle diameter of not more than 15 μm is not less than 40%, which crystalline particles have a degree of crystallinity of not less than 80%.

The present invention further provides the above-mentioned crystalline particles obtained by finely grinding the subject compound or a pharmaceutically acceptable salt thereof with a fluid energy mill or an impact mill.

The present invention further provides a process for producing crystalline particles of N-(17-cyclopropylmethyl-4, 5α-epoxy-3,14-dihydroxy-morphinan-6β-yl)-phthalimide or a pharmaceutically acceptable salt thereof, comprising grinding N-(17-cyclopropylmethyl-4,5α-epoxy-3,14-dihydroxy-morphinan-6β-yl)-phthalimide or a pharmaceutically acceptable salt thereof with a fluid energy mill or an impact mill.

Effects of the Invention

The crystalline finely-ground particles of the subject compound or a pharmaceutically acceptable salt thereof according to the present invention can be a pharmaceutical active substance having a high solubility rate in water and a high bioavailability while ensuring a storage stability. It is expected that the present invention can provide pharmaceutical compositions with an excellent release property and stability.

BEST MODE FOR CARRYING OUT THE INVENTION

Figure 1:
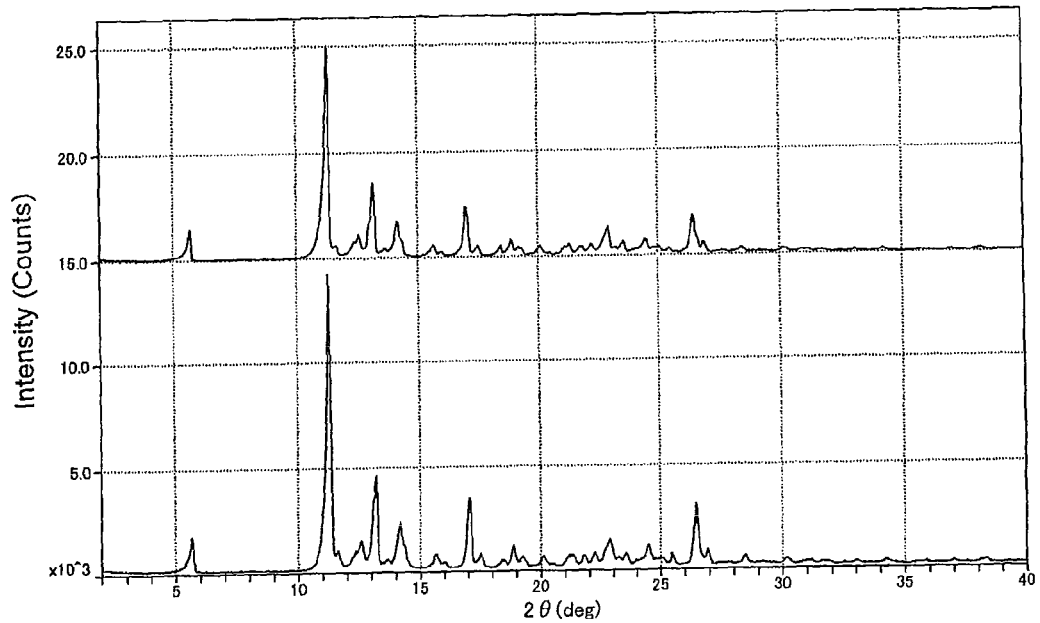
FIG. 1 shows the powder X-ray diffraction patterns of Example 2. The top and bottom of FIG. 1 show the powder X-ray diffraction patterns after and before fine grinding, respectively, taking the diffraction angle 2θ (deg) along the abscissa and the intensity (Counts) along the ordinate.

In the present invention, D50 and D90 are indices for defining particle diameter distribution. Particle diameter distribution is usually called particle size distribution. Particles are divided into groups along with their size with appropriate intervals, and weight (volume) or particle number of the particles belonging to each group is measured to obtain the particle number (frequency) of each group. Taking the particle number (frequency) along the ordinate and taking the particle diameter along the abscissa, a particle diameter distribution is shown as a histogram, frequency curve, cumulative curve or the like. In the present invention, frequency was calculated based on volume. In the particle diameter distribution obtained in such a manner, D50 means the particle diameter at the point where the volume which is cumulatively measured from smaller particles reaches 50%, that is, the point where the cumulative frequency of the volume distribution reaches 50%. D90 means the particle diameter at the point where the volume which is cumulatively measured from smaller particles reaches 90%, that is, the point where the cumulative frequency of the volume distribution reaches 90%. Cumulative frequency (%) of particles which have a smaller diameter than a specified particle diameter can also be calculated from such a distribution chart.

Measurement of the particle diameter distribution of the crystalline finely-ground particles according to the present invention may be carried out with a commercially available apparatus using laser diffraction/scattering based on Mie Theory. For example, the measurement is carried out using a commercially available apparatus such as Malvern (registered trademark) Mastersizer Laser Diffraction Analyzer (Malvern Instruments Ltd). This analyzer irradiates He—Ne laser beam and blue light-emitting diode on particles to obtain a light scattering pattern which occurs on a detector by the irradiation, and then analyzes the light scattering pattern according to Mie Theory to determine the particle diameter distribution. Although the measurement may be carried out by either dry or wet measurement, Evaluation 1 shows the results which were obtained from the dry measurement. An example of the measurement condition is as follows, which was used in Evaluation 1 of the present invention.

Measurement Condition

Apparatus: Laser diffraction-based particle size distribution analyzer Mastersizer 2000 (Malvern)
Dry measurement unit: Scirocco 2000
Refractive Index of Samples: Real part; 1.810, Imaginary part; 0
Time for Sample Measurement: 1 second
Time for Background Measurement: 5 seconds
Pressure: 2.0 bar
Feed Rate: 40%
Analysis Model: Single narrow mode
Calculation Sensitivity Enhanced
Particle Shape Irregular
Analysis Range: 0.020 to 2000 μm
Basis of Size Distribution Measurement: Volume The degree of crystallinity of the crystalline finely-ground particles according to the present invention is calculated from the integrated intensity ratio of crystalline peaks and amorphous halo which are extracted from an X-ray diffraction pattern obtained by powder X-ray diffraction measurement.

In the powder X-ray diffraction measurement, X-ray irradiated on a powder sample forces electrons in the sample material to vibrate, by which X-ray scattering occurs in a coherent manner. Based on the coherently scattered X-rays, diffraction intensity is measured on each diffraction angles. The measured data is expressed as an X-ray diffraction pattern of diffraction intensity versus diffraction angle. An X-ray diffraction pattern of crystalline materials shows sharp triangular peaks which are unique and characteristic to each crystal forms of various compounds. On the other hand, amorphous materials do not have a clear regularity in the structure but have a random molecular orientation, and therefore intensity of coherently diffracted X-rays is weak, which causes a gently-sloping halo with a diffuse maximum. Thus, according to an X-ray diffraction pattern or a degree of crystallinity calculated from an X-ray diffraction pattern, it can be determined whether the sample is a crystalline material or not.

The powder X-ray diffraction measurement may be carried out by using, for example, a powder X-ray diffractometer (2200/RINT Ultima+PC) manufactured by Rigaku as described in Evaluation 2 of the present invention. In preparation of a measurement sample, 100 mg of a sample material is filled in a glass sample plate (0.2 mm depth) in non-destructive condition, and the surface of the sample material is leveled out using a glass plate to obtain a measurement sample. An example of the measurement condition is as follows, which was used in the present invention.

Measurement Condition

| X-Ray Source: | CuKa line Using a curved crystal monochromator (graphite) |
|---|---|
| Output: | 40 kV/50 mA |
| Divergence Slit: | 1/2 deg |
| Soller Slit: | 10 mm |
| Scattering Slit: | 1/2 deg |
| Receiving Slit: | 0.15 mm |
| Detector: | Scintillation counter |
| Scan Mode: | 2θ/θ scan, continuous scan |
| Measurement Range (2θ): | 2 deg to 90 deg |
| Scan Speed (2θ): | 2 deg/min |
| Counting Step (2θ): | 0.02 deg |

The degree of crystallinity may be calculated by a known analysis method using diffraction patterns of a sample material and sample plate alone (without a sample material) and a difference pattern thereof. For example, using a powder X-ray diffraction pattern analysis software JADE5.0 produced by MDI, which is a commercially available analysis software, a degree of crystallinity may be calculated as follows.

Analysis Method (1) A difference pattern of the diffraction patterns of a sample material and sample plate alone is smoothed (Savitzky-Goray filter: 19 points).
(2) For a display area of the difference pattern, the x-axis: diffraction angle (2θ) is set between 2 deg and 90 deg, and the y-axis: diffraction intensity (Counts) is set between 0 and 500.
(3) Points are set at diffraction angles of 0, 65 and 90 deg, respectively, and a straight line parallel to the x-axis is drawn such that the line is contact with the difference diffraction pattern at a range of 65 deg to 90 deg. The area below the line is determined as a background.
(4) The background is subtracted.
(5) An integrated intensity at a range of 4 deg to 60 deg is calculated (which corresponds to a sum of the integrated intensity of crystalline peaks and an amorphous halo: Sc+Sa)
(6) Points are set at diffraction angles of 2, 7, 18, 26, 30, 35, 59, 65 and 90 deg, respectively. At 2, 65 and 90 deg, the diffraction intensity is set as 0, and at 7, 18, 26, 30, 35 and 59 deg, an approximation by a cubic spline is made such that the approximation formula is in contact with the difference pattern obtained after the subtraction of the background, thereby estimating an amorphous halo.
(7) The amorphous halo is subtracted.
(8) The integrated intensity at a range of 4 deg to 60 deg is calculated (which corresponds to the integrated intensity of the crystalline peaks: Sc).
(9) A degree of crystallinity is calculated according to the following equation.

$$Xc = (Sc/(Sc+Sa)) \times 100 \qquad \text{Equation}$$

Xc: Degree of crystallinity (%)
Sc: Integrated intensity of the crystalline peaks
Sa: Integrated intensity of the amorphous halo As the crystalline finely-ground particles of N-(17-cyclopropylmethyl-4,5α-epoxy-3,14-dihydroxy-morphinan-6β-yl)-phthalimide or a pharmaceutically acceptable salt thereof according to the present invention, those having a particle diameter distribution in which D50 is within a range of 1 to 30 μm and D90 is not more than 90 μm are preferred, and those having a particle diameter distribution in which D50 is within a range of 1 to 20 μm and D90 is not more than 60 μm are more preferred, and those having a particle diameter distribution in which D50 is within a range of 3 μm to 15 μm and D90 is not more than 50 μm are especially preferred. Among these, those having a particle diameter distribution in which D50 is within a range of 3 μm to 10 μm and D90 is not more than 30 μm are still more preferred. Alternatively, those having a particle diameter distribution in which the cumulative frequency of the volume distribution occupied by particles having a volume-base particle diameter of not more than 15 μm is not less than 40%, preferably not less than 50%, are preferred. The degree of crystallinity of the particles is not less than 80%, preferably not less than 85%, more preferably not less than 90%.

Particles of organic compounds obtained by a conventional fluid energy type dry grinding process, which is used for fine grinding in the present invention, have D50 of not less than 1 μm. In cases where specific wet grinding processes such as a process using nanomizer are used, which are also known to be used for fine grinding, a fine powder having D50 in nano size can be obtained. However, it is required to separate the media used in grinding from the obtained powder.

The fine grinding process of the present invention is a process by which finely ground particles are obtained while keeping the crystallinity of the subject compound or a pharmaceutically acceptable salt thereof (hereinafter also referred to as "subject compound species"). Fluid energy mills such as a jet mill or impact mills such as a hammer mill are preferably used in the process. It is more preferred that fluid energy mills, especially preferably a jet mill be used in the process.

The properties of the ground products of the subject compound species obtained by the above-mentioned process may be clearly distinguished from the properties of those obtained by a tumbler type grinding process using physical or mechanical friction. When the subject compound species were finely ground using a ball mill, which is a tumbler mill, the degree of crystallinity of the obtained particles were less than 80%, and thus the crystallinity could not kept, which revealed that fine grinding processes using a tumbler mill cannot be used for grinding the subject compound species.

In the fluid energy type, using a fluid energy of the compressed air, a compound is caught in a sonic jet stream which blows at a high speed under high pressure, and ground by the collision of particles of the compound with each other. As the air, not only air at room temperature but also heated hot air and cold air cooled with a liquid nitrogen or the like may be used. As fluid energy type mills generally have greater grinding power than impact type mills, such very fine particles that have D50 of several μm can be obtained. Specific examples of the jet mill include SK Jet-O-Mill [JOM-0101, JOM-0202] (manufactured by Seishin Enterprise), Single Track Jet Mill [FS-4] (manufactured by Seishin Enterprise), Co-Jet (manufactured by Seishin Enterprise), Counter Jet Mill model AFG (manufactured by Hosokawa Micron), and Spiral Jet Mill model AS (manufactured by Hosokawa Micron).

The impact type mills are roughly classified into 3 types, that is, rotating disc type mills, screen mills, and centrifugation type mills. In many cases, particles which can be obtained by these means have D50 of several dozen μm. Rotating disc type mills have a rotating disc as a rotor, which disc comprises pins or edges. When the rotor rotates at a high speed, the pins or edges hit a sample material, and the sample material is ground by being cut, sheared and smashed. Screen mills grind a sample material by cutting and shearing it with hammers rotating at a high speed. Centrifugation mills grind a sample material by the force of impact which occurs when impact plates rotating at a high speed hit the sample material which is being carried in the axial direction by air flow.

Specific examples of the impact mill include a hammer mill [TAW-1]; Fine Impact Mill UPZ ((pin-plate beater: manufactured by Hosokawa Micron), and Atomizer (manufactured by Fuji Paudal).

In the case of SK Jet-O-Mill [JOM-0101], the service condition varies depending on the model of the mill to be used, the batch of the pharmaceutical active substance and the like, and grinding is preferably carried out at a air pressure of 0.2 to 1 Mpa (G), more preferably 0.3 to 0.8 Mpa (G), which is a feed pressure of an unground active substance into the grinding system (hereinafter simply referred to as "feed pressure"). Although the pressure of two grinding air (G) nozzles (independently referred to as G1 nozzle and G2 nozzle for convenience) may be 0 to 1 MPa as they may be closed in some cases, it is usually preferred that the pressure of G nozzles be 0.2 to 0.8 Mpa (G), more preferably 0.3 to 0.7 Mpa (G) during grinding. The nozzle diameter of G1 and G2 nozzles may be appropriately selected depending on the scale of grinding, and preferably 1.0 to 3.0 mmφ, more preferably 1.2 to 2.5 mmφ. The feed rate of the unground pharmaceutical active substance may be selected, depending on the scale of grinding, within such a range that the ground material can be discharged out of the system without blocking. However, the feed pressure of the mill and the pressure of G nozzles may be freely selected regardless of the above-mentioned range, as long as the mechanical strength, safety in operation and the like can be ensured.

Bioavailability (BA) is, according to the glossary of pharmaceutical terms provided by the Pharmaceutical Society of Japan, an index for how much the administered drug (drug product) is incorporated into the systemic circulation and exerts its effects, and expressed by an extent of bioavailability (in cases where the drug is incorporated into the systemic circulation) and a rate of bioavailability. According to 21 CFR 320.1 (Code of Federal Regulations), BA is defined as "the rate and extent to which the active ingredient or active moiety is absorbed from a drug product and becomes available at the site of action". This concept is based on the idea that "pharmacological effects may be assessed by the concentration of the drug at the site of action and the time course of its appearance there". However, it is usually difficult to measure the concentration of the drug at the site of action. Thus, in cases of the drugs which are intended to be absorbed into bloodstream to become available at the site of action, BA is assessed by the plasma concentration and its time course instead of the concentration at the active site and its time course, because the rate and extent to which drugs are absorbed into the bloodstream have strong relevance to the rate and extent to which drugs reach the active site. The rate and extent are assessed by Cmax (Maximum Blood Concentration) in the circulating blood and AUC (Area Under the Curve).

In general, in regard to release property and bioavailability of drugs, there are some cases where immediate release dosage forms of the active substance may be considered to have low risk of inequivalence of bioavailability in human if the dosage forms have such a high release property that not less than 85% of the labeled amount of the drug substance dissolves in 15 to 30 minutes in a dissolution assessment according to, for example, the dissolution test by the paddle method described in the Japanese pharmacopoeia or the US or European Pharmacopoeia (Reference; Guidance for Industry: Waiver of In Vivo Bioavailability and Bioequivalence Studies for Immediate-Release Solid Oral Dosage Forms Based on a Biopharmaceutics Classification System. U.S. FDA (CDER) August 2000). Based on this view, in the present invention, test tablets containing lactose and magnesium stearate, which are included in the representative additives of solid dosage forms, were prepared, and the dissolution rate of the test tablets was assessed in accordance with the paddle method (paddle speed: 50 rpm) described in the Japanese pharmacopoeia. Tablets showing the release property that not less than 85% of the labeled amount of the active substance dissolved in 15 to 30 minutes were considered to have a release property high enough to ensure the prescribed pharmacological effects.

It should be understood that, although the subject compound N-(17-cyclopropylmethyl-4,5α-epoxy-3,14-dihydroxy-morphinan-6β-yl)-phthalimide per se has already been disclosed together with its synthesis method (Non-patent Literature 1) and may be easily synthesized by a known method, the synthesis method thereof is not restricted thereto. For example, the unground pharmaceutical active substance of the subject compound species may be obtained by the method described in Comparative Example 2 below, and the crystalline finely-ground particles of the present invention may be produced by using it. Preferred examples of the pharmaceutically acceptable salt include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferred, but the salt is not restricted thereto.

The crystalline finely-ground particles of the present invention and the pharmaceutical composition containing the particles as an effective ingredient may be used as a pharmaceutical, for example, as a therapeutic or prophylactic agent for urinary frequency or urinary incontinence, an antipruritic, an analgesic, a therapeutic or prophylactic agent for functional bowel disorder such as irritable bowel syndrome, and an antitussive.

In cases where the particles of the present invention are clinically used as a drug, the drug may consist of only the particles of the present invention, or may appropriately contain additives such as vehicles, stabilizers, preservatives, buffering agents, solubilizers, emulsifiers, diluents, and isotonic agents. The drug may be produced by a conventional method appropriately using these pharmaceutical carriers. Administration modes thereof include oral preparations such as tablets, capsules, granules, powders and syrups; parenteral preparations such as injection solutions, suppositories and solutions; and topical preparations such as ointments, creams and patches. These compositions may be produced in accordance with conventional methods.

The pharmaceutical composition containing the particles of the present invention as an effective ingredient may preferably contain the particles of the present invention in an amount of 0.00001 to 90% by weight, more preferably 0.0001 to 70% by weight. Although the administration dose may be appropriately selected depending on the symptom, age, body weight, administration method and the like, the dose of the effective component per adult per day may be 0.1 μg to 1 g in the case of administration by injection, 1 μg to 10 g in the case of oral administration, and may be administered at one time or dividedly in several times.

EXAMPLES

The present invention will now be described practically by way of Examples and Comparative Examples thereof. The term "unground pharmaceutical active substance" as used in the Examples and Comparative Examples below refers to the unground pharmaceutical active substance of N-(17-cyclopropylmethyl-4,5α-epoxy-3,14-dihydroxy-morphinan-6β-yl)-phthalimide (Compound 1) obtained in Comparative Example 2.

Examples 1 to 5 and Comparative Example 1

Grinding with Fluid Energy Mill (1)

The unground pharmaceutical active substance was ground using SK Jet-O-Mill (JOM-0101: manufactured by Seishin Enterprise). The air pressure and the nozzle diameter were set, as grinding conditions, as shown in Table 1. The feed amount of unground pharmaceutical active substance and the amount of the obtained ground pharmaceutical active substance were also shown in Table 1.

TABLE 1

Grinding with SK Jet-O-Mill

|  |  | Example 1 | Example 2 | Example 3 | Example 4 | Example 5 | Comparative Example 1 |
|---|---|---|---|---|---|---|---|
| Air Pressure | Feed Pressure [Mpa (G)] | 0.50 | 0.50 | 0.30 | 0.40 | 0.60 | 0.40 |
|  | G1 Pressure [Mpa (G)] | 0.45 | 0.45 | 0.30 | STOP | 0.60 | STOP |
|  | G2 Pressure [Mpa (G)] | 0.45 | 0.45 | 0.30 | 0.40 | 0.60 | STOP |
| Nozzle Diameter | G1 [mmφ] | 2.2 | 2.2 | 1.9 | — | 1.9 | — |
|  | G2 [mmφ] | 2.2 | 2.2 | 1.9 | 1.9 | 1.9 | — |
| Feed Amount of Unground Pharmaceutical Active Substance [g] |  | 467 | 196 | 100 | 288 | 600 | 299 |
| Amount of Obtained Ground Pharmaceutical Active Substance [g] |  | 435 | 159 | 75.6 | 251 | 454 | 221 |

Example 6

Grinding with Fluid Energy Mill (2)

The unground pharmaceutical active substance was ground using a jet mill pulverizer Co-Jet (α-mkII: manufactured by Seishin Enterprise). Under the nozzle pressure of 0.5 MPa, 10 g of the unground pharmaceutical active substance was fed into the jet mill and ground over 2 minutes.

Example 7

Grinding with Fluid Energy Mill (3)

The unground pharmaceutical active substance was ground using Single Track Jet Mill (FS-4: manufactured by Seishin Enterprise). The air pressure was set, as a grinding condition, as shown in Table 2. The feed amount of the unground pharmaceutical active substance and the amount of the obtained ground pharmaceutical active substance were also shown in Table 2.

TABLE 2

Grinding with Single Track Jet Mill

|  | Example 7 |
|---|---|
| Air Pressure [Mpa(G)] | 0.45 |
| Feed Amount of Unground pharmaceutical active substance [g] | 160 |
| Amount of Obtained Ground pharmaceutical active substance [g] | 130 |

Example 8 to 9

Grinding with Impact Mill

The unground pharmaceutical active substance was ground using a hammer mill (TASM-1). The mesh size and the speed of rotation were set, as grinding conditions, as shown in Table 3. The feed amount of unground pharmaceutical active substance and the amount of the obtained ground pharmaceutical active substance were also shown in Table 3.

TABLE 3

Grinding with Hammer Mill

| Batch Number of Ground Pharmaceutical Active Substance | Example 8 | Example 9 |
|---|---|---|
| Mesh Size [mmφ] | 1.0 | 0.5 |
| Speed of Rotation [rpm] | 12000 | 12000 |
| Feed Amount of Unground pharmaceutical active substance [g] | 100 | 100 |
| Amount of Obtained Ground pharmaceutical active substance [g] | 81 | 83 |

Comparative Example 2

Production of Unground Pharmaceutical Active Substance of N-(17-Cyclopropylmethyl-4,5α-epoxy-3,14-dihydroxy-morphinan-6β-yl)-phthalimide (Compound 1)

Compound 1

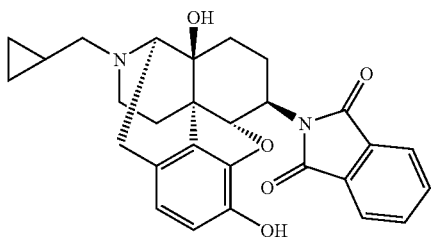

(1) Production of Crude Crystals

To 3.52 kg of 6β-naltrexamine and 20.1 kg of acetic acid, 1.68 kg of phthalic anhydride was added, and the resulting mixture was stirred at an inner temperature of 85-90° C. for 4 hours under nitrogen atmosphere. After cooling the reaction solution to 25° C., 81.3 kg of THF and an aqueous sodium carbonate solution (a solution of 21.2 kg of sodium carbonate in 85.0 kg of water) were added thereto, and the mixture was stirred for 1 hour, followed by neutralization. To the reaction mixture, 44.0 kg of ethyl acetate and 23.6 kg of THF were added to extract it. The organic layer was washed with 31.0 kg of water, and then concentrated under reduced pressure to distill off 109 kg thereof. To the residue, 42.6 kg of ethyl acetate was added, and the mixture was concentrated under reduced pressure. This operation was repeated 8 times to carry out azeotropic dehydration. Thereafter, 42.6 kg of THF was added to the residue and the mixture was concentrated under reduced pressure. This operation was repeated 4 times to replace the solvent with THF. To the residue, 50.7 kg of THF was added, and the resulting mixture was stirred at an inner temperature of 50-60° C. for 30 minutes, followed by filtration through filter paper to remove foreign matter. To the residual solution, 49.3 kg of ethyl acetate was added, and the mixture was concentrated under reduced pressure to distill off 102 kg thereof. To the residue, 42.6 kg of ethyl acetate was added, and the mixture was concentrated under reduced pressure. This operation was repeated 4 times. The generated crystals were recovered by filtration and washed with 7.7 kg of ethyl acetate. The washed crystals were dried under vacuum to obtain 4.0 kg of crude crystals of Compound 1.

(2) Production of Unground Pharmaceutical Active Substance

A mixture of 35.2 kg of crude crystals of Compound 1 and 2347 kg of 2-butanol was heated to reflux for 1 hour under nitrogen atmosphere, and then concentrated under normal pressure while heating the mixture to distill off 1802 kg of 2-butanol. The concentrated mixture was cooled to room temperature over 3 hours, and then stirred for 1 hour. The generated crystals were recovered by filtration and washed with 42.3 kg of 2-butanol. The washed crystals were dried under vacuum to obtain 34.1 kg of unground pharmaceutical active substance of Compound 1.

Comparative Example 3

Grinding with Tumbler Mill (1)

Figure 2:
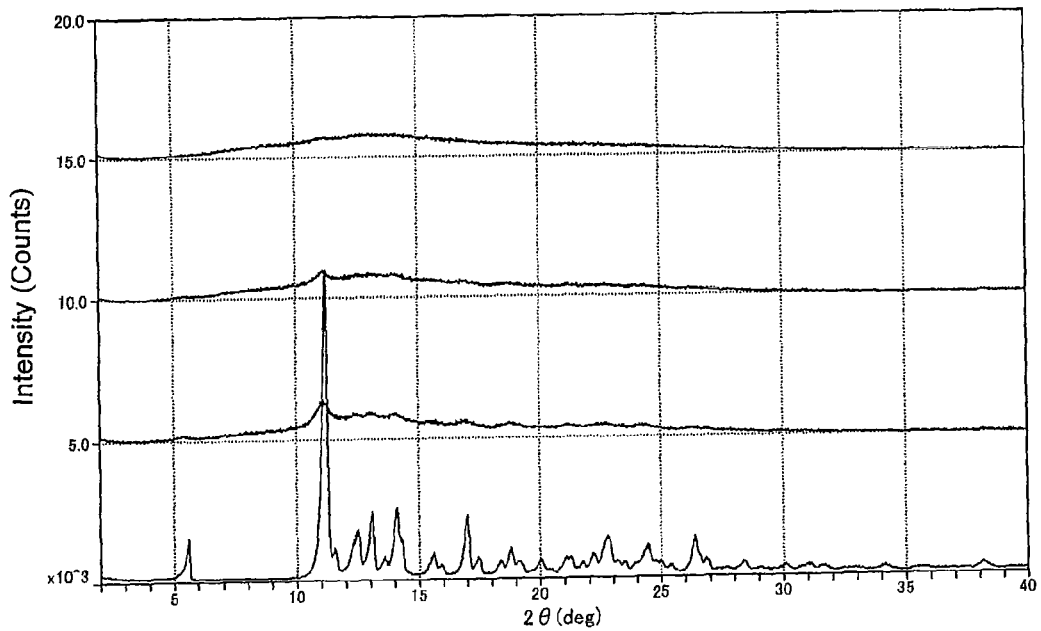
FIG. 2 shows the powder X-ray diffraction patterns of Comparative Example 3. The bottom, second bottom, second top and the top of FIG. 2 show the powder X-ray diffraction patterns before and 1, 3 and 8 hours after fine grinding, respectively, taking the diffraction angle 2θ (deg) along the abscissa and the intensity (Counts) along the ordinate.

Using Table Ball Mill (model V-2M: manufactured by Irie Shokai), which is a tumbler mill, 22.4 g of the unground pharmaceutical active substance was ground. Aliquots of the powder were sampled 1, 3, and 8 hours after grinding, and the samples were subjected to powder X-ray diffraction measurement. The results are shown in FIG. 2. Sharp peaks of X-ray diffraction disappeared as time passed after grinding. Eight hours after grinding, X-ray diffraction peaks were not found and an amorphous halo was observed, indicating that the ground active substance were converted into an amorphous material.

Comparative Example 4, 5, and 6

Grinding with Tumbler Mill (2)

Using Table Ball Mill (model V-2M: manufactured by Irie Shokai), which is a tumbler mill, 10 g of the unground pharmaceutical active substance was ground over 3 minutes (Comparative Example 4), 6 minutes (Comparative Example 5) or 7 minutes (Comparative Example 6). The ground products of the active substance obtained in this experiment, adhering to the inner wall of the mill and the surface of the balls, showed a heavy aggregation as the time of grinding treatment increased.

Comparative Example 7

The unground pharmaceutical active substance was ground using mortar and pestle.

Evaluation 1: Measurement of Particle Diameter Distribution

The particle diameter distribution of the subject compound was measured by dry measurement using a particle size distribution analyzer (Mastersizer 2000, manufactured by Malvern). D50 and D90 were calculated as an index of the particle diameter distribution.

Evaluation 2: Check of Crystalline State and Measurement of Crystallinity

For check of the crystalline state and measurement of the degree of crystallinity, powder X-ray diffraction measurement was carried out using a powder X-ray diffraction analyzer (2200/RINT Ultima+PC) manufactured by Rigaku.

Powder X-ray diffractions of the ground pharmaceutical active substances obtained in Examples 1 to 9 were measured to find that all the ground pharmaceutical active substances which were ground with a fluid energy mill or impact mill had a sharp X-ray diffraction pattern with a retained crystal form. The powder X-ray diffraction pattern of Example 2 is shown in FIG. 1 as a representative chart. The degree of crystallinity is shown in Table 4 below. It was confirmed that all the ground pharmaceutical active substance had a crystallinity of not less than 80%. The results of the particle diameter distribution measurement are also shown in Table 4. All the ground pharmaceutical active substances obtained by methods described in Examples 1 to 9 had D50 within a range of 1 to 20 μm and D90 of not more than 60 μm.

TABLE 4

Measured Particle Diameter Distribution and Crystallinity of Pulverized Pharmaceutical Active Substance

| | Particle Diameter Distribution | | Degree of |
|---|---|---|---|
| | D50 (μm) | D90 (μm) | Crystallinity (%) |
| Example 1 | 4.25 | 9.14 | 89 |
| Example 2 | 6.23 | 12.4 | 89 |
| Example 3 | 9.89 | 29.4 | 94 |

TABLE 4-continued

Measured Particle Diameter Distribution and Crystallinity of Pulverized Pharmaceutical Active Substance

| | Particle Diameter Distribution | | Degree of |
|---|---|---|---|
| | D50 (μm) | D90 (μm) | Crystallinity (%) |
| Example 4 | 14.6 | 47.8 | 96 |
| Example 5 | 7.83 | 16.0 | 90 |
| Example 6 | 5.13 | 11.2 | 88 |

TABLE 4-continued

Measured Particle Diameter Distribution and Crystallinity of Pulverized Pharmaceutical Active Substance

| | Particle Diameter Distribution | | Degree of |
|---|---|---|---|
| | D50 (μm) | D90 (μm) | Crystallinity (%) |
| Example 7 | 5.67 | 16.1 | 87 |
| Example 8 | 11.8 | 35.3 | 92 |
| Example 9 | 11.5 | 30.9 | 89 |

The particle diameter distribution and the degree of crystallinity of the pharmaceutical active substance obtained in Comparative Examples 1 to 7 are shown in Table 5.

TABLE 5

Measured Particle Diameter Distribution and Crystallinity

| | Particle Diameter Distribution | | Degree of |
|---|---|---|---|
| | D50 (μm) | D90 (μm) | Crystallinity (%) |
| Comparative Example 1 | 32.4 | 110 | 97 |
| Comparative Example 2 | 64.0 | 173 | 93 |
| Comparative Example 4 | 17.1 | 168 | 82 |
| Comparative Example 5 | 19.2 | 246 | 71 |
| Comparative Example 6 | 23.0 | 436 | 61 |
| Comparative Example 7 | — | — | 73 |

Evaluation 3: Storage Stability (1)

For comparison of storage stability, the ground pharmaceutical active substance of Example 6 (crystallinity 88%) which was ground with a jet mill pulverizer Co-jet (α-mkII: manufactured by Seishin Enterprise) and that of Comparative Example 7 (crystallinity 73%) which was ground with a mortar and pestle were left under the storage condition of 60° C./75% RH opened, and the content of the pharmaceutical active substance was analyzed by HPLC 0.5 and 2 months after the start of the storage (Table 6). As a result, compared to that of Example 6, the ground pharmaceutical active substance of Comparative Example 7 with a low crystallinity showed a remarkable decrease in the content of pharmaceutical active substance as time passed from the start of the storage, and its storage stability was largely lowered. Thus, it was revealed that there is a large difference in the stability of crystalline finely-ground particles of the subject compound on the border between particles with a crystallinity of 73% and 88%.

TABLE 6

Storage Stability

| | | At Start of Storage | 0.5-Month Later | 2-Month Later |
|---|---|---|---|---|
| Ground Pharmaceutical Active Substance of Example 6 (Crystallinity 88%) | Content of Pharmaceutical Active Substance by HPLC (%) | 99.39 | 99.15 | 99.09 |
| | Degree of Decrease Based on Start of Storage | — | 1.39 | 1.49 |
| Ground Pharmaceutical Active Substance of Comparative Example 7 (Crystallinity 73%) | Content of Pharmaceutical Active substance by HPLC (%) | 99.30 | 98.85 | 98.51 |
| | Degree of Decrease Based on Start of Storage | — | 1.64 | 2.13 |

Degree of Decrease = (100 − Content of pharmaceutical active substance after storage(%))/(100 − Content of pharmaceutical active substance at start of storage(%))

Evaluation 4: Storage Stability (2)

For comparison of storage stability, the ground pharmaceutical active substance of Comparative Example 4 (grinding for 3 min), Comparative Example 5 (grinding for 6 min) and Comparative Example 6 (grinding for 7 min), all of which were ground with Table Ball Mill (model V-2M: manufactured by Irie Shokai), were left under the storage condition of 60° C./75% RH opened, and the total amount of related substances was analyzed by HPLC 0.5 and 2 months after the start of the storage (Table 7). As a result, the ground pharmaceutical active substance with a higher crystallinity had fewer related substances 0.5 and 2 month later and thus had a better storage stability. In particular, Comparative Example 4 had an excellent storage stability with not more than 1.00% of related substances 2 month later. Thus, it was revealed that there is a large difference in the stability of crystalline finely-ground particles of the subject compound on the border between particles with a crystallinity of 71% and 82%.

TABLE 7

Storage Stability

| Pharmaceutical Active Substance | Degree of Crystallinity (%) | Total Amount of Related Substances (%) | | |
|---|---|---|---|---|
| | | At Start of Storage | 0.5-Month Later | 2-Month Later |
| Comparative Example 4 | 82 | 0.23 | 0.38 | 0.59 |
| Comparative Example 5 | 71 | 0.24 | 0.61 | 1.07 |
| Comparative Example 6 | 61 | 0.24 | 0.67 | 1.27 |

Evaluation 5: Evaluation of Dissolution Rate

Figure 3:
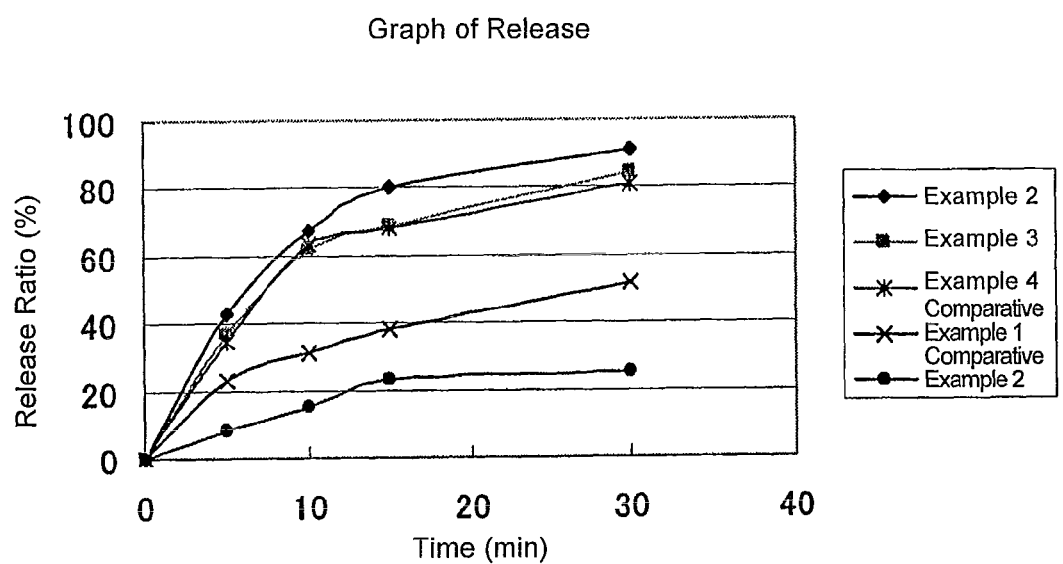
FIG. 3 shows a graph of the release obtained in the evaluation of the dissolution rate in Evaluation 5. Data of Example 2, Example 3, Example 4, Comparative Example 1, and Comparative Example 2 are shown in order from top to bottom, taking the time (min) along the abscissa and the release ratio (%) along the ordinate.

For evaluation of dissolution rate, test tablets were prepared using the pharmaceutical active substance with a different particle diameter distribution (Example 2, Example 3, Example 4, Comparative Example 1, and Comparative Example 2), and a dissolution test was performed on the test tablets. The dissolution test was carried out in accordance with the Japanese pharmacopoeia, 14th Edition, Dissolution Test 2nd, Paddle Method, using pH 6.0 phosphate buffer as a test fluid at 50 rpm. The release ratio was measured 5, 10, 15, 30 minutes after the start of the test and calculated by HPLC method. FIG. 3 shows a graph of release ratio versus time course. The results show that the pharmaceutical active substances of Examples 2, 3 and 4 had a release ratio of not less than 80% 30 minutes later, which was higher than the release ratio of the pharmaceutical active substances of Comparative Examples 1 and 2, and thus had a high dissolution rate of the pharmaceutical active substance.

Table 8 shows D50 and D90 of the particle diameter distribution of the used pharmaceutical active substance, and the cumulative frequency (%) of the volume distribution which was occupied by particles with volume-based particle diameter of not more than 15 (μm). These results revealed that there is a large difference in the dissolution rate of the crystalline finely-ground particles of the subject compound on the border between particles with D50 of 14.6 μm and 32.4 μm, and on the border between particles with D90 of 47.8 μm and 110 μm. As for the cumulative frequency (%) of the volume distribution which is occupied by particles with a volume-based particle diameter of not more than 15 (μm), it was also revealed that there is a large difference in the dissolution rate of the crystalline finely-ground particles of the subject compound on the border between particles with the cumulative frequency (%) of 23.3% and 51.7%.

TABLE 8

Release Ratio (%) and Particle Diameter Distribution

| Pharmaceutical Active Substance | Particle Diameter Distribution | | Cumulative Frequency of Volume Distribution Which Is Occupied by Particles with Volume-Based Particle Diameter 15 (μm) or Less (%) |
|---|---|---|---|
| | D50 (μm) | D90 (μm) | |
| Example 2 | 6.23 | 12.4 | 96.3 |
| Example 3 | 9.89 | 28.4 | 70.8 |
| Example 4 | 14.6 | 47.8 | 51.7 |
| Comparative Example 1 | 32.4 | 110 | 23.3 |
| Comparative Example 2 | 64.0 | 173 | 9.4 |

The test tablets were prepared as follows. That is, 10 mg of the pharmaceutical active substance, 119.35 mg of lactose (DMV, Pharmatose 200M) and 0.65 mg of magnesium stearate (Taihei Chemical Industrial) were gently mixed such that the crystals of the active substance should not be broken, and 130 mg of the obtained physical mixture was compressed at 70 kgf/cm$^2$ for 15 seconds to form test tablets.

Evaluation 6: Plasma Concentration of Drugs when Administered to Dogs

The pharmaceutical active substances with a different particle diameter distribution (Example 2 and Comparative Example 2) were orally administered (10 mg/kg) to 3 male beagle dogs, and blood samples were collected at each time points to measure the drug concentration in plasma. The pharmacokinetic parameters are shown in Table 9. The results show that, compared to the pharmaceutical active substance (Example 2) with a small particle diameter, the pharmaceutical active substance (Comparative Example 2) with a large particle diameter had a low AUC and C max, which indicates that the drug concentration in plasma was low. The particle diameter distribution of the used pharmaceutical active substances is shown in Table 9. The results revealed that there is a difference in bioavailability between particles with D50 of 6.23 μm and those with 64.0 μm, and between particles with D90 of 12.4 μm and those with 173 μm, indicating that such particles that are ground more finely are preferred.

TABLE 9

| | Drug Plasma Concentration, Average (Standard Deviation) | | Particle Diameter Distribution | |
|---|---|---|---|---|
| | AUC 0-24 h (ng · hr/mL) | C max (ng/mL) | D50 (μm) | D90 (μm) |
| Example 2 | 180.3 (40.9) | 18.4 (7.2) | 6.23 | 12.4 |
| Comparative Example 2 | 44.5 (25.4) | 4.8 (1.8) | 64.0 | 173 |

The invention claimed is:

1. Crystalline particles of N-(17-cyclopropylmethyl-4,5α-epoxy-3,14-dihydroxy-morphinan-6β-yl)-phthalimide or a pharmaceutically acceptable salt thereof, having a particle diameter distribution in which a particle diameter (D50) at the point where cumulative frequency of volume distribution cumulatively calculated from particles having a smaller diameter reaches 50% is within a range of 1 to 30 μm, and a particle diameter (D90) at the point where cumulative frequency of volume distribution cumulatively calculated from particles having a smaller diameter reaches 90% is not more than 90 μm, which crystalline particles have a degree of crystallinity of not less than 80%.

2. The crystalline particles according to claim 1, which are crystalline particles of N-(17-cyclopropylmethyl-4,5α-epoxy-3,14-dihydroxy-morphinan-6β-yl)-phthalimide.

3. The crystalline particles according to claim 1 or 2, having a particle diameter distribution wherein D50 is within a range of 1 to 20 gm and D90 is not more than 60 μm.

4. The crystalline particles according to claim 1 or 2, having a particle diameter distribution in which D50 is within a range of 3 to 15 μm and D90 is not more than 50 μm.

5. The crystalline particles according to claim 1 or 2, having a particle diameter distribution in which D50 is within a range of 3 to 10 μm and D90 is not more than 30 μm.

6. Crystalline particles of N-(17-cyclopropylmethyl-4,5α-epoxy-3,14-dihydroxy-morphinan-6β-yl)-phthalimide or a pharmaceutically acceptable salt thereof, having a particle diameter distribution in which cumulative frequency of volume distribution occupied by particles having a volume-base particle diameter of not more than 15 μm is not less than 40%, which crystalline particles have a degree of crystallinity of not less than 80%.

7. The crystalline particles according to claim 6, which are crystalline particles of N-(17-cyclopropylmethyl-4,5α-epoxy-3,14-dihydroxy-morphinan-6β-yl)-phthalimide.

8. The crystalline particles according to claim 1, obtained by finely grinding crystalline N-(17-cyclopropylmethyl-4,5α-epoxy-3,14-dihydroxy-morphinan-6β-yl)-phthalimide or a pharmaceutically acceptable salt thereof with a fluid energy mill or an impact mill.

9. The crystalline particles according to claim 1, obtained by finely grinding crystalline N-(17-cyclopropylmethyl-4,5α-epoxy-3,14-dihydroxy-morphinan-6β-yl)-phthalimide with a fluid energy mill or an impact mill.

10. A process for producing crystalline particles of N-(17-cyclopropylmethyl-4,5α-epoxy-3,14-dihydroxy-morphinan-6β-yl)-phthalimide or a pharmaceutically acceptable salt thereof, comprising grinding N-(17-cyclopropylmethyl-4,5α-epoxy-3,14-dihydroxy-morphinan-6β-yl)-phthalimide or a pharmaceutically acceptable salt thereof with a fluid energy mill or an impact mill.

11. A process for producing crystalline particles of N-(17-cyclopropylmethyl-4,5α-epoxy-3,14-dihydroxy-morphinan-6β-yl)-phthalimide, comprising grinding N-(17-cyclopropylmethyl-4,5α-epoxy-3,14-dihydroxy-morphinan-6β-yl)-phthalimide with a fluid energy mill or an impact mill.

12. The process for producing crystalline particles according to claim 10 or 11, comprising grinding at feed pressure of 0.2 to 1 Mpa using a fluid energy mill.

* * * * *